United States Patent [19]
Chelmicka-Schorr et al.

[11] Patent Number: 5,264,459
[45] Date of Patent: Nov. 23, 1993

[54] USE OF β-ADRENERGIC AGONISTS TO TREAT PATIENTS WITH DEMYELINATING OR AUTOIMMUNE DISEASES

[75] Inventors: Ewa E. Chelmicka-Schorr; Barry G. W. Arnason, both of Chicago; Anthony T. Reder, Oak Park; Louis Cohen, Chicago, all of Ill.

[73] Assignee: ARCH Development Corporation, Chicago, Ill.

[21] Appl. No.: 913,673

[22] Filed: Jul. 13, 1992

[51] Int. Cl.$^5$ .......................................... A61K 31/135
[52] U.S. Cl. ..................................................... 514/646
[58] Field of Search ....................................... 514/646

[56] References Cited

PUBLICATIONS

Beushausen, S., et al., "In Vivo and In Vitro Models of Demyelinating Disease: Activation of the Adenylate Cyclase System Influences JHM Virus Expression in Explanted Rat Oligodendrocytes," *Journal of Virology*, 61(12):3795–3803, 1987.
Chelmicka-Schorr, E., et al., "The β-Adrenergic Agonist Isoproterenol Suppresses Experimental Allergic Encephalomyelitis in Lewis Rats," *Journal of Neuroimmunology*, 25:203–207, 1989.
Chelmika-Schorr, E., et al., "Treatment with β-Adrenergic Agonist Isoproterenol Protects Against Development of Experimental Allergic Encephalomyelitis (EAE) in Rats," *Neurology*, 39(Suppl 1):330, 1989, Abstract p. 510.
Hoffman, Brian B., and Robert J. Lefkowitz, "Catecholamines and Sympathomimetic Drugs," In: *Goodman and Gilman's the Pharmacological Basis of Therapeutics*, Eighth Edition, pp. 187–220, 1990.
Karaszewski, Joseph W. et al., "Sympathetic Skin Responses Are Decreased and Lymphocyte Beta-Adrenergic Receptors Are Increased in Progressive Multiple Sclerosis," *Annals of Neurology*, 27(4):366–372, 1990.
Kirby, J. D. T. et al., "Prostacyclin Increases Cyclic-Nucleotide Responsiveness of Lymphocytes from Patients with Systemic Sclerosis," *The Lancet*, pp. 453–454, 1980.
Dialog Search Report.
Brosnan et al., "Prazosin, An $\alpha_1$-Adrenergic Receptor Antagonist, Suppresses Experimental Autoimmune Encephalomyelitis in the Lewis Rat," *Proceedings of the National Academy of Science, USA*, 82:5915–5919, 1985.
Chelmicka-Schorr and Arnason, "Nervous System-Immune System Interactions," In: *Immunologic Mechanisms in Neurologic and Psychiatric Disease*, B. H. Waksman, ed., Raven Press, New York, pp. 67–90, 1990.
Chelmicka-Schorr et al., "Sympathetic Nervous System (SNS) and Macrophage Function," Presented at 4th International Workshop on Neuroimmunomodulation, May, Florence, Italy, 1990.
Goldmuntz et al., "Prazosin Treatment Suppresses Increased Vascular Permeability in Both Acute and Passively Transferred Experimental Autoimmune Encephalomyelitis in the Lewis Rat," *The Journal of Immunology*, 137(11):3444–3450, 1986.
Karaszewski et al., "Increased Lymphocyte Beta-Adrenergic Receptor Density in Progressive Multiple Sclerosis is Specific for the CD8+, CD28-Suppressor Cell," *Annals of Neurology*, 30(1):42–47, 1991.
Levine et al., "Suppression of Experimental Allergic Encephalomyelitis by Stress," *Proceedings of the Society of Experimental Biological Medicine*, 109:294–298, 1962.
Reder et al., "Sympathetic Nervous System Involvement in Immune Responses of Mice and in Patients with Multiple Sclerosis," In: *Neuroimmune Networks: Physiology and Diseases*, E. J. Goetzl, Ed., Alan R. Liss, New York, pp. 137–147, 1989.

*Primary Examiner*—S. J. Friedman
*Attorney, Agent, or Firm*—Arnold, White & Durkee

[57] ABSTRACT

The present invention discloses improved methods for the treatment of autoimmune diseases using β-adrenergic agonists, and particularly, $\beta_2$-adrenergic agonists. The treatment of animals with either EAE or EAN using the $\beta_2$-adrenergic agonist terbutaline significantly suppressed clinical disease. A Phase I safety treatment trial with terbutaline was conducted in MS patients. Twenty-four patients were treated for 4 weeks. No obvious side effects were observed. At 4 weeks, 15 of the 24 patients improved on neurologic rating scale and 17 patients reported subjective improvement. Treatment of rats with EAMG, an animal model of the autoimmune disease myasthenia gravis, is also demonstrated to alleviate disease symptoms.

9 Claims, No Drawings

USE OF β-ADRENERGIC AGONISTS TO TREAT PATIENTS WITH DEMYELINATING OR AUTOIMMUNE DISEASES

The government may own rights in the present invention pursuant to NIH grants 2 RO1 NS18413-07A1 and PO1NS-24575-03.

BACKGROUND OF THE INVENTION

1. Field of the Invention

The present invention relates to improved methods for the treatment of demyelinating or autoimmune diseases. The invention relates to the use of β-adrenergic agonists, and particularly, $\beta_2$-adrenergic agonists such as terbutaline, in the treatment of patients with autoimmune demyelinating diseases such as multiple sclerosis, post-infectious encephalomyelitis, acute inflammatory demyelinating polyradiculoneuropathy or other autoimmune diseases such as myasthenia gravis.

2. Description of the Related Art

In multiple sclerosis (MS), the host nervous system is attacked by its own immune system. White blood cells invade the central nervous system (CNS) damaging oligodendrocytes and causing demyelination and glial scarring. The etiology of MS is unknown but the observed damage to oligodendrocytes and to CNS myelin is believed to result from the amplification of multiple immune responses. The amplified immunological reactions of this disease produce clinical symptoms which vary depending upon the location of CNS damage (i.e. demyelination or "plaques"). Abnormalities of immune function occur in MS in both the CNS and in the blood. Mononuclear cells are activated, B cells secrete excessive immunoglobulin, and T cell suppressor functions are reduced (Reder & Arnason, 1985).

Interactions between the nervous system and the immune system are well documented and suggest that the sympathetic nervous system (SNS) is involved in regulating immune function. Lymphoid tissues are extensively innervated, and lymphocytes and monocytes possess adrenergic receptors for neurotransmitters released by the SNS (Giron et al., 1980; Reilly et al., 1976; Williams et al., 1981; Felten et al., 1987a; 1987b). Furthermore, the immune system exerts an effect on the nervous system through lymphokines and monokines, suggesting that regulation between these two systems may involve a feedback loop. Such feedback regulation would involve effects on the immune system being mediated by neurotransmitter binding to adrenergic receptors on lymphocytes, and effects on the nervous system being mediated through the action of lymphokines and monokines upon neurons (Murphy et al., 1980; Kreueger et al., 1984; Fierz et al., 1985).

There is evidence of impaired sympathetic nervous system function in patients with MS. Patients with MS have decreased variation in heart rate in response to Valsalva manoeuver and decreased sweating (Noronha et al., 1968; Cartlidge, 1972; Neubauer & Gundersen, 1978; Chagnac et al., 1986; Pentland & Ewing, 1987; Nordenbo, 1988). Karaszewski et al. (1990) recently reported that the sympathetic skin response (SSR), a measure of the function of the autonomic nervous system, was absent in 54% of 24 patients with active progressive MS, but present in all 24 normal controls ($p < 0.001$). These data showed that a significant number of patients with chronic progressive MS have compromised sympathetic sudomotor function. Other studies have also shown SNS function to be deficient in MS (Senaratne et al., 1984; Sterman et al., 1985). Defective function of SNS in patients with MS may contribute to immune derangement and severity of the illness.

Other studies also show that destruction of the SNS enhances many immune response (Miles et al., 1981a; 1981b; Miles, 1984; Miles et al., 1984). The inventors have shown that the severity of experimental allergic encephalomyelitis (EAE), an autoimmune disease which serves as a model for MS, is significantly increased in adult rats chemically sympathectomized as newborns (Chelmicka-Schorr et al., 1988; Chelmicka-Schorr et al., 1989a; 1989b). Additionally, the inventors have recently shown that passively transferred EAE is more severe in sympathectomized recipients as well as in recipients of cells from sympathectomized animals compared to control recipients or recipients of cells from donors with an intact SNS (Chelmicka-Schorr et al., 1991b).

The basis for immune system enhancement in animals with an ablated SNS is not fully understood. One possibility might be that catecholamines normally secreted by the SNS bind to β-adrenergic receptors on lymphocytes and macrophages, increase intracellular CAMP and thereby down regulate immune responses (Giron et al., 1980; Hadden, 1975; Lefkowitz et al., 1981). In sympathectomized animals, immune responses are enhanced presumably secondary to low levels of cAMP. Since β-adrenergic agonists cause levels of cyclic nucleotides within lymphocytes to rise, elevated levels of cAMP would tend to inhibit lymphocyte proliferation and thereby act to suppress immune function. Whereas the β-adrenergic agonist isoproterenol suppresses the severity of EAE, the β-adrenergic antagonist propranolol augments somewhat the severity of EAE (Chelmicka-Schorr et al., 1989b). Although these findings are consistent with isoproterenol's effect occurring through β-adrenergic receptors, it must be stressed that the mechanism of action of isoproterenol in immune diseases is as yet not totally understood.

The present inventors determined that treatment with the β-adrenergic agonist isoproterenol suppresses the severity of experimental allergic encephalomyelitis (EAE). Although the prior art has reported positive effects of β-adrenergic agonists in animal models as well as increases in the number of $\beta_2$-adrenergic receptors on lymphocytes in humans with chronic progressive MS and experimental animals with EAE (Chelmicka-Schorr et al., 1988; Chelmicka-Schorr et al., 1989a; Karaszewski et al., 1990; Karaszewski et al., 1991; Mackenzie et al. 1989), the effect of $\beta_2$-adrenergic agonists have not been tested in animal models or humans.

Myasthenia gravis is an autoimmune disease which involves macrophage and antibody-mediated attack at neuromuscular junctions. The defective neuromuscular transmission results in voluntary muscle fatigability and weakness. Although not demyelinating, myasthenia has some similarities with MS in that it represents an impairment of both immune and nervous system functions. A useful animal model for myasthenia gravis also exists in rats, this is experimental autoimmune myasthenia gravis (EAMG). In common with MS, despite some knowledge of myasthenia, understanding of its aetiology and pathogenesis in humans is imperfect.

Unfortunately, current treatment strategies for demyelinating and autoimmune diseases are relatively ineffective. For example, MS is often treated with corticosteroids, despite the fact that there is no clear evidence that they influence the course of the disease over the long term. ACTH can, however, be used to some effect to aid the recovery from an acute exacerbation. Interferon α treatment has also been investigated, but is not recommended due to immunological side effects, and also because improvements were observed in patients given placebo during such trials (McFarlin, 1985). Due to the inefficiencies and drawbacks of the drugs investigated to date, the current advice available for MS patients is sadly limited and includes the avoidance of fatigue and emotional stress.

The treatment options available for patients with myasthenia gravis are somewhat better than those for MS patients, but are still far from satisfactory. Current treatments include thymectomy, plasmapheresis and the administration of immunosuppressive drugs. Most commonly, patients are treated with either anticholinesterases or corticosteroids, despite the side effects of sweating, salivation, abdominal cramps, diarrhoea and weakness with the former, and weight gain, hyperglycemia, cataracts, bone damage and stomach ulcers associated with the latter. Furthermore, the dosage schedule for treatment with anticholinesterases is extremely variable and the length of time recommended for corticosteroid treatment is only one to three years.

As discussed above, treatment for patients with MS and treatment for myasthenia gravis is imperfect. Without a clear understanding of the disease etiology or mechanism, or suitable methods for identifying useful agents for treatment, the development of effective treatment agents has been thwarted. Due to these circumstances and the severity of MS and myasthenia, there is accordingly an urgent need for treatments which will be effective in suppressing the effects of these diseases in humans.

SUMMARY OF THE INVENTION

The present invention addresses one or more shortcomings or disadvantages in the available treatment regimens for demyelinating or autoimmune diseases such as multiple sclerosis (MS) and myasthenia gravis, through the use of β-adrenergic agonists. In preferred embodiments, the invention contemplates the use of $\beta_2$-adrenergic agonists, and particularly terbutaline, as agents to treat patients with MS or myasthenia.

In certain embodiments, the present invention concerns a method for treating a demyelinating or autoimmune disease by the application of a therapeutically effective dose of a β-adrenergic agonist, and preferably a $\beta_2$-adrenergic agonist such as terbutaline, to human subjects with the disease. As used herein, the term "treating a disease by the application of a therapeutically effective dose of a β-adrenergic agonist" is used to signify that the β-adrenergic agonist is supplied to the patient in amounts, and for a period of time, that are effective to provide improvement in one or more of the clinically measured parameters of the disease.

Several demyelinating diseases are proposed to be treatable by the β-adrenergic agonists of the present invention, such as post-infectious encephalomyelitis and inflammatory demyelinating polyneuropathy. The inventors contemplate that the β-adrenergic agonists will be particularly useful in treating multiple sclerosis, as the drug is effective in EAE, an animal model of MS. An autoimmune disease which is considered to be particularly suitable for treatment with β-adrenergic agonists is myasthenia gravis, although other autoimmune diseases such as post-infectious encephalomyelitis and acute inflammatory demyelinating polyradiculoneuropathy may also be treated in this manner.

To determine whether there has been an improvement in one or more of the clinically measured parameters of the disease, one would determine the value of such a parameter in a given patient both before and during treatment. Various clinical signs and symptoms are known by those are known by those of skill in the art to be suitable as markers of disease severity For example, the relative severity of MS may be categorized by the Kurtzke Disability Status Scale in Multiple Sclerosis (Kurtzke et al., 1983). Additionally, the Scripps Neurological Rating and the Ambulation Index are known to be used to determine MS severity. For myasthenia gravis, the Osserman rating scale is frequently used as a measure of disease severity (Osserman et al., 1958).

A particular advantage of the present invention is that it involves a novel application and use of agents that are already in use clinically in the treatment of various other disorders and ailments. By utilizing compounds that have already been approved for clinical use in other disorders, the present inventors have provided safe agents for use in new treatment strategies against the above diseases and disorders. Accordingly, $\beta_2$-adrenergic agonists considered to be of use in the present invention include metaproterenol, albuterol, isoetharine, pirbuterol, bitolterol, or ritodrine, and preferably, terbutaline. The inventors propose that the β agonists may be administered to the patient in any pharmaceutically acceptable vehicle and by any route heretofore acceptable for these agents. The preferred route of administration is orally, although one may, if desired, choose to administer the agonists intravenously, sublingually, or in a sustained release form.

As will be understood by those skilled in the art, the effective doses of the agonists will depend upon the route of administration and the patient's sensitivity to the particular β or $\beta_2$-adrenergic agonist. Using the preferred oral route of administration, recommended doses range from about 1.0 to about 10.0 mg, and preferably, from about 2.0 to about 5.0 mg, and even more preferably, from about 1.25 to about 2.5 mg, given three times per day either daily or every other day. However, it will be appreciated that the dosages may be more effectively adjusted as the severity of the disease varies from patient to patient.

DETAILED DESCRIPTION OF THE PREFERRED EMBODIMENTS

The novel method of this invention comprises the treatment of patients diagnosed as having a demyelinating or autoimmune disease with a β-adrenergic agonist, and preferably, with a $\beta_2$-adrenergic agonist. This method comprises the administering of an effective amount of a β- or $\beta_2$-adrenergic agonist to patients diagnosed as having such as disease, for example, multiple sclerosis (MS) or myasthenia gravis. Even more particularly, the method of the present invention comprises the administration of an effective amount of the $\beta_2$-adrenergic agonist terbutaline to patients with such diseases.

Terbutaline is known to be an agent of use as a bronchodilator for treating or controlling asthma as well as a uterine relaxant in premature labor. To date, there has been no information as to its use in the treatment of demyelinating or autoimmune diseases. The present inventors herein disclose that this drug is effective in the treatment of such disorders, and particularly, in the treatment of multiple sclerosis. Other $\beta_2$-adrenergic agonists useful in this novel method of treatment include: metaproterenol, albuterol, isoetharine, pributerol, bitolterol, and ritodrine.

The adrenergic agonists of the present invention may be administered to a patient in a dosage form selected from the group consisting of pills, tablets, capsules, caplets, solutions, suspensions, syrups, suppositories, and aerosols. Additionally, the dosage of the $\beta$- or $\beta_2$-adrenergic agonist used may be in a sustained-release form to cause the action of such agonist to persist over a more prolonged period of time. Such sustained-release formulations are well known to those skilled in the art.

The adrenergic agonists may be administered in various salt forms. For example, the following are commercially available: metaproterenol sulfate as "Alupent" (Boehringer Ingelheim) or "Metaprel" (Dorsey); terbutaline sulfate as "Brethaire" or "Brethine" (Ciba-Geigy) or "Bricanyl" (Merrell-Dow); albuterol sulfate as "Proventil" (Schering-Plough) or "Ventolin" (Glaxo); isoetharine hydrochloride as "Bronkosol" (Sterling)(Parke-Davis) or isoetharine mesylate as "Bronkometer" (Sterling); pributerol acetate as "Maxair"; bitolterol mesylate as "Tornalate" (Sterling); or ritodrine hydrochloride as "Pre-Par" (Philips-Duphar) or "Yutopar" (Astra).

The dosage form of agonists may be administered by various routes including sublingual, oral, intravenous, rectal, or subcutaneous. Therapeutically effective doses of particular agonists and the frequency of dosage administration are to be determined according to protocols understood by those skilled in the art. In one embodiment of the present invention method, therapeutically effective dosages of terbutaline are from about 1.0 to 5.0 mg administered two or more times per day. More particularly, terbutaline doses may comprise about 1 0 to 2.5 mg administered two or more times per day. In a preferred embodiment of the present invention method, terbutaline is administered in tablet form daily or on alternate days in doses of about 1.25 to 2.5 mg three times per day.

The exact mechanism by which the $\beta$- or $\beta_2$-adrenergic agonists exert a suppressive effect on demyelinating or autoimmune diseases (e.g., MS and myasthenia gravis) is unknown. However, the inventors postulate that $\beta_2$-adrenergic agonists inhibit immune response through elevating intracellular cAMP levels. In this manner, $\beta_2$-adrenergic agonists are believed to be likely to provide a similar suppressive effect on the excessive immune response found in other demyelinating or autoimmune diseases which are similar to multiple sclerosis or myasthenia gravis, respectively. By inhibiting immune response through elevating intracellular CAMP levels in lymphocytes, $\beta_2$-adrenergic agonists are believed to be likely to provide a similar suppressive effeot on the excessive immune response found in other diseases which are similar to multiple sclerosis. Thus, the $\beta_2$-adrenergic agonists of the present treatment method may be useful in treating other demyelinating disease, such as post-infectious encephalomyelitis.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I $\beta_2$-Adrenergic Agonist (Terbutaline) Suppression of EAE in Rats 1. Methods Lewis rats with experimental allergic encephalomyelitis (EAE), a model of MS, were used to examine the action of the $\beta_2$-adrenergic agonist terbutaline. EAE is known to be induced in rats by the administration of substances containing myelin or myelin basic protein (MBP). In this case, seven to eight week old Lewis rats were immunized intradermally with 20% crude guinea pig brain and spinal cord homogenate in CFA.

EAE-suffering rats were treated with terbutaline in 1 ml phosphate buffered saline (PBS) freshly prepared each day at a dose of 300 µg twice daily intraperitoneally (i.p.) from the day of immunization and continuing throughout the experiment. Control rats were injected with 1 ml PBS alone using the same schedule.

Animals were examined daily for the severity of disease, which was assessed as: 0=no illness; (+1)=tail weakness; (++2)=paraplegia; and (+++3)=tetraplegia and death. The sum of scores of clinical EAE in each rat from the first day of illness until recovery was used to express the severity of EAE. Statistical analyses were conducted using Students, t-test.

If required, histological examinations can be conducted as follows. Fix sections of the brains and spinal cords with formalin and paraffin and stain with hematoxylin and eosin. Examine coronal sections of the brain and transverse sections of the spinal cord at multiple levels. Histological lesions can be scored as: 0=no lesions observed; (+1)=average of 1 lesion per section; (++2) average of 2-6 lesions per section; and (+++3)=average of more than 6 lesions per section.

2. Results

Treatment with terbutaline was observed to suppress clinical EAE significantly. The mean of the peak of illness severity was 4.6±0.5 (n=54) for terbutaline-treated rats and 6.5±0.6 (n=57) for control rats. The difference was statistically significant at p<0.001 (Student's t test).

EXAMPLE II

Phase I Trial of $\beta_2$-Adrenergic Agonist (Terbutaline) in MS Patients

1. Methods

Patients

Twenty-four MS patients were treated in this study. Twelve patients were treated with 5 mg doses and twelve others with 2.5 mg doses of terbutaline administered orally in tablet form three times per day.

Detailed cardiovascular evaluations were conducted both before and during this phase I study. The patients were assessed at zero, one, four, and eight weeks. Various clinical parameters were measured allowing their scores on the neurologic rating scale to be determined (See Appendix One). The patients, subjective feelings as to their state of health were also recorded.

Study of β-adrenergic receptor density on peripheral blood lymphocytes

Peripheral blood was drawn by venipuncture into heparinized 15 ml vacutainer tubes. Mononuclear cells were isolated on Ficol gradient (Karaszewski et al., 1990). Cells Were washed 3× with Hank's Balanced Sal Solution (HBSS). [$^{125}$I]cyanopindolol ([$^{125}$I]CYP) of Specific activity 2,200 Ci/mmol was used as a specific $\beta_2$-receptor radioactive ligand. To determine total binding, $5 \times 10^5$ cells were incubated with at least 8 different concentrations of [$^{125}$I]CYP in 300 µl of buffer containing 150 mM sodium chloride, 1 mM ascorbic acid and 20 mM Tris for 90 min at 30° C. Specific binding of [$^{125}$I]CYP was determined by incubating the cells using the same concentration range of [$^{125}$I]CYP as for total binding in the presence of high concentration (6 µM) of unlabeled β-adrenergic antagonist propranolol. Specific activity was defined as the amount of [$^{125}$I]CYP displaced by high concentration of unlabeled propranolol. The association rate constant was determined by incubating splenocytes with [$^{125}$I]CYP in a time range from 0 to 360 min. To study the dissociation rate constant after 90 min of incubation of splenic cells with [$^{125}$I]CYP, 6 µM of dl-propranolol were added and incubation continued to 360 min. During 360 min of incubation multiple samples were studied for specific binding to establish association and dissociation curves. The incubations were terminated by dilution with 5 ml of ice-cold buffer, and cells with bound ligand were separated by rapid filtration through a Whatman CF/C glass fiber filter. The filters were washed again with ice-cold incubation buffer and counted in a Beckman gamma 4000 scintillation counter.

Binding kinetics were analyzed by the Scatchard method using the LIGAND computer program. The maximal number of binding sites (B max) and the equilibrium dissociation constant ($K_D$) for the β-adrenergic receptors on splenocytes were determined. Counts per minute were expressed in molar equivalents. Rate constants were determined by the computer program KINETIC.

2. Results

At four Weeks, 15 of 24 patients had improved on the neurologic rating scale, and 7 had worsened. Subjective improvement was reported by 17 patients at 4 weeks and worsening by 2 patients. There were no significant cardiovascular symptoms in terbutaline-treated MS patients except for increased pulse rate from 77/min at baseline to 87/min at 1 and 4 weeks. Patients had no substantial complaints.

$\beta_2$-adrenergic receptor density was measured on CD8+ lymphocytes and was shown to decrease from 3.5+/−0.6 fmole receptors per million CD8+ cells at baseline to 1.8+/−0.3 at 1 and 4 weeks of treatment. The difference was significant at p<0.0005. The number of receptors returned to the baseline four weeks after treatment was terminated. There was no difference of any measure between patients treated with 5 mg three times per day (tid) and patients treated with 2.5 mg tid.

Patients who improved on terbutaline in the phase I trial were anxious to resume taking this medication because the quality of their lives deteriorated following the discontinuation of treatment. This phase I trial has thus been extended by continuing to treat those MS patients who improved with terbutaline treatment. The continued treatment with terbutaline is at a dose of 2.5 mg tid given every other day or at a dose of 1.25 mg tid given every day.

Although the results of this extension of the study have not been determined, the lower doses of terbutaline are anticipated to still bring improvement but may prevent lowering of $\beta_2$-adrenergic receptors on lymphocytes and desensitization to treatment. Results of this extended treatment at lower dosages are to be evaluated after twelve months. All patients who entered this study had detailed cardiovascular workups done before and during the first part of the phase I trial. Patients who entered this study extension, as before, met the criteria of no history of angina, myocardial infarction, arrhythmia, significant orthostatic hypotension, thyroid disease, infection, or pregnancy and had blood pressure readings between 160/90 and 90/60.

EXAMPLE III

Prophetic Phase II Trial of $\beta_2$-Adrenergic Agonist (terbutaline) Treatment in MS Patients Although the methods used in this example outline the approach currently being used to study the effect of terbutaline in human patients with multiple sclerosis, the methodology described below is intended to illustrate the present inventors, approach to testing other $\beta_2$-adrenergic agonists which are effective in treating patients with demyelinating diseases.

Terbutaline is commonly used in the treatment of bronchial asthma, premature labor, and chronic obstructive pulmonary disease. When used in these ways, at doses of up to 5 mg three times a day, terbutaline is known to exert few side effects. The most commonly observed side effects to date include tremor, dizziness, weakness, and sweating. Less common side effects, typically associated with stimulation of the $\beta_2$ receptor, have also been observed, for example, palpitations, tachycardia, headache, flushing of the skin, cardiac dysrhythmias, and angina. Myocardial necrosis has been reported after large doses.

The phase I trial showed that MS patients tolerated 5 mg terbutaline doses three times a day without detrimental side effects. This prompted further studies of longer term treatment to be conducted.

The inventors have planned a double-blind, placebo-controlled phase II study to evaluate the therapeutic effect of the $\beta_2$-adrenergic agonist terbutaline on the course of relapsing/remitting (RR) and chronic/-progressive (CP) multiple sclerosis (for a discussion of RR and CC forms, see Weiner et al., 1983; Schumacher et al. 1965).

Two groups of fifty patients will be studied: (a) patients with chronic progressive MS who demonstrated a 2-point decline on the Kurtzke et al. (1983) rating scale during the preceding 2 years and who are not higher than 5.5 on the scale; and (b) patients with relapsing/remitting MS, who had at least 4 exacerbations in the preceding two years. Exacerbations are defined, according to the criteria of Weiner & Ellison (1983), as a "development of a new sign or group of signs or worsening of existing sign(s) in a patient who has been stable or has improved with in the last month. The exacerbation must be accompanied by objective neurological changes. The patient must be suffering an exacerbation for at least 7 days but no more than 8 weeks" (Weiner & Ellison, 1983). Chronic/progressive MS will be defined, following the modified criteria of Weiner & Ellison (1983), as "the development of increasing disability signs and symptoms" without improvement for 2 years.

Eligible patients will be selected from a Neurology clinic population. To be eligible for enrollment in the study, each patient must firstly meet the following Inclusion Criteria. Secondly, they must not have any contra-indication for treatment with $\beta_2$-adrenergic agonists or other conditions which would interfere with participation in the study, as listed in the following Exclusion Criteria.

Inclusion Criteria

1. Patients must have clinically definite MS (Poser criteria; Poser et al., 1983).
2. Patients will be between 21 and 55 years of age inclusive.
3. Patients with relapsing/remitting MS must have a history of at least 4 exacerbations in preceeding two years and not be higher than grade 5.5 and the Kurtzke ratings scale.
4. Patients with chronic/progressive MS must have demonstrated at least a 2 point decline on the Kurtzke rating scale over the proceeding 2 years and be in the 3 to 5.5 range on the scale.
5. Women capable of childbearing must use adequate contraceptive measures.
6. Patients must read and sign the IRB-approved informed consent statement at the end of the screening visit.

Exclusion Criteria

1. Pregnancy or lactation.
2. Medical or psychiatric condition that compromises the patient's ability to give informed consent or complete the study.
3. Patients who test seropositive for human immunodeficiency virus 1.
4. Patients who have blood pressure below 90/60 or above 160/90.
5. Patients who have a history of angina, myocardial infarction, arrhythmia, orthostatic hypotension or any other cardiovascular disease.
6. Patients who have thyroid disease, asthma or infections.
7. Patients who have had ACTH or glucocorticoid therapy during the previous 2 months.
8. Patients who have had cytotoxic therapy during the previous year.
9. Patients who have a history of chronic or debilitating illness which could interfere with participation in the study.

At a screening visit after the patient has been informed about all aspects of the study and a detailed history of the patient has been obtained, the patient will have a neurological examination using (1) Kurtzke Disability Status Scale in multiple sclerosis (KurtZke et al, 1983); (2) Functional neurological status evaluation; (3) Scripps neurology rating scale; and (4) Ambulation Index. These methods will be known to those of skill in the art in light of the present specification, and are further presented in Appendix One. The patient will also have a cardiological examination, EKG, Holter monitoring, CBC, Chem-17 and urinalysis.

Patients eligible for enrollment into the study will be treated with terbutaline or placebo at a dose of 2.5 mg three times a day for a period of 24 months. Each group of patients (RR or CP) will be randomly divided in two using a table of random numbers and assigned treatment with either terbutaline or placebo.

An automated process will be used to whole-tablet encapsulate either terbutaline or placebo into identical capsules. The capsules will be backfilled with incipient material as recommended by the PDR to stabilize the tablets within the capsules. The study biostatistician will prepare a list of sequential treatment assignments for each stratum (i.e., CP and RR) using the RAND (1955) table of random numbers. A permutated-block randomization (Lachin et al., 1988) will be employed with variable block size. These lists will be used by the capsule manufacturer to prepare the corresponding sequences of medication bottles, each containing either terbutaline or placebo. Once enrolled, the patient's name will be written on the bottle of medication. These bottles will be kept by a study nurse, and the appropriate amount of medication given to the patients at each clinic visit. A tear-off label will be transferred from the bottle to a case report form and kept in the study file. In case of emergency, these can be opened to reveal the medication a patient is taking.

Patients in the study will have neurological examinations performed during the study at 1, 3, 6, 12, 18 and 24 months. The neurological evaluation will be conducted by a physician in a double-blinded fashion using the same criteria as above: (1) Kurtzke Disability Status Scale in multiple sclerosis (Kurtzke et al., 1983); (2) Functional neurological status evaluation; (3) Scripps neurology rating scale; and (4) Ambulation Index; See Appendix One. Self-evaluation questions will also be included, these assess the patients own "sense of wellbeing" as follows. MS patients will report fluctuations from day to day, describing their days as "good days" or "bad days." Patients will record their perception of the day in the late afternoon once a week according to the following scale:

1. Very good day.
2. Good day.
3. Averaqe day.
4. Bad day.
5. Very bad day.

Laboratory tests will also be conducted including: CBC, Chem-17 and urinalysis at 12 and 24 months, and EKG with rhythm strip at 1, 6, 12, is, and 24 months after entry into the study. Pattern reversed visual evoked potentials (VEP), a measure of visual system function, will be performed on the day of entry into the study, before onset of treatment, and then at 3, 6, 12 and 24 months.

In examining VEP, at least two replications of 128 alternations of B/W checkerboard patterns containing 30' and 15' checks will be obtained from each eye. The amplified EEG (1-300 Hz bandpass) will be derived from occipital scalp ($O_2$) referenced to frontal scalp ($F_2$) with a forehead ground. The subjects will view the 10 deg. by 12 deg. screen from 1.5 m wearing their usual correction. The subject's pupil size and visual acuity will be obtained, along with any visual complaints. The latency and amplitude of the first major positive deflection of the response (P100) will be recorded for each condition. Repeated-measure analysis-of-variance will be used to identify group differences. Individual increases in latency that are beyond 99th percentile will be tabulated.

Sympathetic skin responses to electrical stimulation, a measure of postganglionic sudomotor function, will also be conducted on the day of entry into the study. In measuring the sympathetic skin response, all patients will be studied in the supine position and skin temperatures will be maintained above 32° C. The standard electromyograph disc electrode will be attached to the sole and dorsum of the right foot. A recording will be obtained from an EMG (TECA TE4) with a frequency response from 1.6 Hz to 3.2 kHz. Amplification sensitivity will be set between 50 and 500 μV/division and sweep speed will be 500 msec/division. Stimulation consisting of square pulses of 200 μsec duration will be delivered to the skin. Absence of pedal sympathetic skin responses will be considered an indicator of impaired sudomotor function.

The $\beta_2$-adrenergic receptor density on lymphocytes and the function of suppressor cells will be conducted on the day of entry into the study and then at 6 months. The $\beta_2$-adrenergic receptor density will be determined as described above. The function of suppressor cells will be studied by ConA suppressor assay. Briefly, mononuclear cells (MNCs) will be isolated from peripheral blood on a Ficol-hypaque density gradient. The cells will be washed three times at 4° C. with Hanks' Balanced Salt Solution (HBSS) plus 1% fetal bovine serum and suspended at $10_6$ cells per ml in RPMI 1640 medium supplemented with 10% fetal bovine serum, gentamicin (0.1 mg/ml) and glutamine (4 mM/100 ml). 5–10 cc aliquots of cells will then be cultured in 25 cm$_2$ plastic flasks either with 5 μg/ml of ConA (suppressor or S-cells) or without (control of C-cells). After 48 hours of incubation, both the S- and C-cell fractions will be treated with mitomycin C (50 μg/ml) for 30 minutes. All S- or C-cells will then be washed ×4 and resuspended in culture medium at 106 cells per ml. Fresh responder cells (R-cells), isolated from a control donor(s), will also be washed and resuspended at $10_6$ cells/ml. Microwell cultures consisting of 0.1 ml of each of the cells listed below will then be established and incubated for 72 hours.

Combination A = R cells + S cells + ConA (3 μg/ml)

Combination B = R cells + C cells + ConA (3 μg/ml)

Cultures will be harvested on a PHD cell harvester after a 5-hour pulse with 1 μCi$^3$H-thymidine per well and counts per minute (cpm) will be determined.

$$\% \text{ suppression} = 1 - \frac{\text{cpm}(A)}{\text{cpm}(B)} \times 100\%$$

During the study, patients will also return to the clinic for examination during exacerbations or at the onset of adverse symptoms. For the duration of the treatment period, each patient will be urged to contact the study nurse immediately should any symptoms suggestive of exacerbation appear. The patient will be examined by the neurologist, and ACTH therapy will be given at the discretion of the physician. Treatment with ACTH will be carried out as follows:

| DAYS | DOSAGE |
|---|---|
| 1–3 | Aqueous ACTH 80 units in 500 ml of 5% dextrose in water IV over 8 hours each day |
| 4–10 | ACTH gel 40 units IM twice daily |
| 11–13 | ACTH gel 35 units IM twice daily |
| 14–16 | ACTH gel 30 units IM twice daily |
| 17–19 | ACTH gel 50 units IM once daily |
| 20–22 | ACTH gel 40 units IM once daily |
| 23–25 | ACTH gel 30 units IM once daily |
| 26–28 | ACTH gel 20 units IM once daily |
| 30, 32, 34 | ACTH gel 20 units IM on each day, then discontinue |

The study will be completed in four years. After 24 months of treatment, the medication will be gradually discontinued over a period of 4 months. Statistical analyses will be conducted using the methods described in Appendix Two. Criteria for early withdrawal from the study are listed below.

Early Withdrawal Criteria

1. Interruption of scheduled dosing for greater than three weeks unless a result of exacerbation.
2. Patient's decision to discontinue treatment because of adverse symptoms or for any other reason.
3. Physician's decision to discontinue treatment because of adverse effects: diastolic blood pressure falls below 85% of baseline; if significant orthostatic hypotension, angina, chest pain, resting t achycardia of >110/min, or supraventricular ventricular arrhythmia develop, or for any other appropriate reason.
4. Loss of patient to follow-up.
5. Pregnancy.
6. Poor compliance.
7. Unauthorized use of concomitant therapy.

EXAMPLE IV $\beta_2$-Adrenergic Agonist (Terbutaline) Suppression of Acute Passive-Transfer EAMG in Rats The following example illustrates the effect of treating animals having autoimmune disease with a $\beta$-adrenergic agonist. More particularly, it illustrates the effect of treating animals with acute passive-transfer EAMG, a model of myasthenia gravis, with the $\beta_2$-adrenergic agonist terbutaline.

Experimental autoimmune myasthenia gravis (EAMG) is an animal model for the disease myasthenia gravis. In both the animal model and the human disorder, the disease is caused by a defective neuromuscular transmission which results in fatigability and weakness of voluntary muscles.

EAMG can be induced in animals by immunization with purified acetylcholine receptor (AChR) in adjuvants (Lennon et al., 1975; Tarrab-Hazdai et al., 1975). If Bordetella pertussis is used as an additional adjuvant, the illness is biphasic. One week after immunization, animals develop acute illness and four weeks later, after recovery from the initial episode, they develop a chronic form of the disease (Lennon et al., 1976). Passive transfer EAMG induced by an injection of monoclonal antibody (mAb) against AChR produces acute illness which mimics acute EAMG produced with immunization. Acute passive transfer EAMG peaks at 24–48 hours after injection of mAb and is followed by recovery 3–4 days later (Lindstrom et al., 1976; Lennon et al., 1980). The inventors have shown that ablation of the SNS in experimental animals augments immune responses and augments the experimental autoimmune diseases allergic experimental encephalomyelitis (EAE) and EAMG (Chelmicka-Schorr et al., 1988; Agius et al., 1987).

1. Methods

Monoclonal Antibody

Monoclonal antibody 132A (mAb 132A), a rat IgG 2a specific for the α subunit of AChR, was used in this study to induce acute passive-transfer EAMG. Hybridoma cell lines producing anti-AChR antibody were prepared as described below. Briefly, Lewis rats were immunized with AChR from Torpedo californica. Three weeks after immunization, spleen lymphocytes were fused with the mouse myeloma cell line P3-X63Ag8 and hybrids selected by culturing in medium containing HAT.

The mAb 132A, prepared from tissue culture supernatant fluid, was purified to homogeneity by ion exchange chromatography as analyzed by SDS-PAGE. Binding to AChR was assessed by ELISA using alkali-stripped Torpedo AChR membrane antigen. Purified, concentrated mAb 132A was sterilized by filtration through a 0.22 nm membrane (Amicon) and stored at $-20°$ C. Aliquots of the same batch of 132A were used throughout the study (Gomez et al., 1979).

Introduction of acute passive-transfer EAMG with mAb 132A

Four-week-old female Lewis rats were injected with 2 mg/kg of body weight of mAb 132A by intracardiac route. Animals were examined every 24 hours. Clinical disease was assessed as: 0=no disease; 1=weak grip, defined as inability to grasp and lift an empty mouse cage top; 2=abnormal, wobbly gait; 3=inability to walk forward more than one or two steps; 4=total paralysis, defined as inability to rise to upward posture.

Treatment with $\beta_2$-adrenergic agonist terbutaline

Twenty-eight (5 experiments) experimental rats were injected IP with terbutaline at a dose of 300 μg in 1 ml of PBS twice daily for four days, starting two days ($-2D$) before injection of mAb 132A and continuing for two days after injection ($+2D$). Thirty (5 experiments) control rats were injected IP with 1 ml of PBS using the same injection schedule as for terbutaline. Peak severity of illness in each animal (scale 0–4) was used to calculate results of treatment. Statistical analyses were done using Student's test.

Electrophysiologic studies

Recordings of the electromyographic (EMG) responses to repetitive nerve stimulation were performed in vivo on the muscles of the wrist flexor compartment using subcutaneous active and ground electrodes. The recording electrodes were connected to the input of a preamplifier of a Teka Model B-2 Electromyograph. A bipolar stimulation electrode was inserted through the skin of the axilla into the region of the brachial plexus. A needle through the skin distal to the stimulating electrode served as the ground or reference electrode. The output signal from the preamplifier was connected to a Tektronix 2A60 amplifier and Model 565 oscilloscope and the responses photographed from the screen. The stimulating electrode was positioned to optimize the EMG response to supramaximal stimulation.

The percent of decrement at 3 Hz at 140% supramaximal stimulation was determined as follows: amplitude of the first response minus amplitude of the fifth response/amplitude of the first response. EMG was performed 24 hours after injection of mAb 132A. Six experimental and 6 control rats from two experiments were studied. Statistical analyses were done using Student's t test.

Histology of the neuromuscular junction

Immediately following electrophysiological evaluation, wrist flexor muscle was obtained from the contralateral forelimb. The muscle was frozen in isopentane cooled in liquid nitrogen. Cryostate sections (8 μm) were stained for acetylcholinesterase to localize the endplates and acid phosphatase to identify acid phosphatase-containing mononuclear inflammatory cells (Yam et al., 1971). The muscle endplates were evaluated using light microscopy. The pathological findings in the endplate region were separation of the endplate from the underlying muscle cell membrane, positive staining for acid-phosphatase, or both. At least 100 endplates were evaluated for each rat studied.

2. Results

Acute passive transfer EAMG was found to be significantly less severe in animals treated with terbutaline. Twenty-four hours after injection of mAb 132A the severity of illness of rats treated with terbutaline was $0.95\pm0.15$ (n=28) versus $1.83\pm0.18$ (n=30) in controls (5 experiments). The difference was significant at a p value of $<0.001$. Forty-eight hours after injection of antibody the disease was still less severe in treated animals as compared to the control group; however, the difference was not statistically significant.

Decremental EMG responses in response to repetitive stimulation were observed in all terbutaline-treated and control rats. The decrement was more severe in the control group; $21\pm8\%$ as compared to $17\pm1.0\%$ in the treated group. The difference was not statistically significant. The most striking difference, however, was the amplitude of the first compound muscle action potential (CMAP), which was significantly smaller in the control group as compared to terbutaline-treated rats. The CMAP amplitude was $3.4\pm1.0$ mV in control versus $20.1\pm12.6$ mV in experimental group. The difference was significant at a p value of 0.03. The reduction of the first CMAP correlates directly with the severity of the clinical illness of human myasthenia gravis (Desmedt, 1981a-c) and of acute passive transfer EAMG in rats.

Analysis of the histologic changes of the end plate region of studied muscle induced by the mAb 132A showed that both groups, control and terbutaline-treated, had the same degree of inflammation as determined by the same number of acid phosphatase-positive mononuclear positive cells present in the endplate regions in both groups.

EXAMPLE V $\beta_2$-Adrenergic Agonist (Terbutaline) Suppression of EAN in Rats This example presents results from controlled studies to examine the effects of treating animals having experimental allergic neuritis (EAN) with the $\beta$-adrenergic agonist terbutaline. EAN serves as an experimental model for human acute inflammatory demyelinating polyradiculoneuropathy (AIDP). Results from studies on EAN are therefore proposed to be directly applicable to human treatment regimens for patients with AIDP.

In EAN, activated macrophages most likely play a major role in damaging peripheral nerve myelin. The inventors postulated that treatment with $\beta$-adrenergic agonists would suppress EAN by inhibiting immune responses, suppressing macrophage activation, and by replacing in part a malfunctioning SNS in this disease.

As shown below, it was found that treatment of EAN rats with terbutaline does unequivocally suppress EAN.

1. Methods

To produce EAN, 6, 7 or 8 week-old female rats may be injected with an appropriate amount of bovine peripheral nerve homogenate (such as 0.1 ml of 20% homogenate) emulsified in CFA in a hind foot pad. For the following studies, the inventors chose to immunize 8-week-old female Lewis rats for EAN by subcutaneously injecting 2.5 mg of peripheral nerve myelin in 50 µl of CFA in one hind foot pad.

From the day of immunization, 6 rats were treated with terbutaline i.p. 600 µg twice daily, 5 times/week, and 5 control rats were injected with saline using the same schedule. The rats were examined daily and weighted 5 times/week. The time of onset and the severity of EAN between β-adrenergic agonist-treated and control rats was compared using clinical, electrophysiologic and histological criteria.

2. Results

The first symptoms of clinical EAN were noted on the 12th day postimmunization. Clinical EAN was scored on a scale of 0-5. The severity of clinical EAN was expressed as a sum of scores from daily evaluations of each rat. Treatment with terbutaline was found to unequivocally suppress EAN. The mean clinical score for terbutaline-treated rats was $3.5 \pm 1.5$ (n=6) as compared to $25.8 \pm 5.9$ (n=5) for the saline-treated control group. The difference was statistically significant at p=0.001.

The rats were also studied electrophysiologically. The amplitude of distal CMAP in terbutaline-treated rats was $13.6 \pm 5.4$ mV (n=6) as compared to $6.38 \pm 3.2$ mV (n=5) in controls. The conduction block (CMAP P/D ratio 0.7 or less) was observed in 3 out of 5 saline-treated and only in 1 out of 6 terbutaline-treated EAN rats. The conduction velocity measured in the sciatic nerve as $44.3 \pm 5.0$ m/sec (n=6) in terbutaline-treated and $29.4 \pm 1.1$ (n=5) in control EAN rats. The difference was statistically significant at p=0.01.

These results therefore indicate that treatment with the β-adrenergic agonist terbutaline suppresses EAN. This treatment is thus proposed to be an advantageous method of treating human patients with acute inflammatory demyelinating polyradiculoneuropathy (AIDP).

APPENDIX ONE

KURTZKE DISABILITY STATUS SCALE IN MULTIPLE SCLEROSIS
A Mental Function grade of 1 does not enter into FS scores for KDS steps.

- ☐ 0.0 = Normal neurological exam (all grade 0 in Functional Status [FS]).
- ☐ 1.0 = No disability, minimal signs all in one FS (i.e., grade 1).
- ☐ 1.5 = No disability, minimal signs in more than one FS (more than one grade 1).
- ☐ 2.0 = Minimal disability in one FS (one FS grade 2, others 0 or 1).
- ☐ 2.5 = Minimal disability in two FS (two FS grade 2, others 0 or 1).
- ☐ 3.0 = Moderate disability in one FS (one FS grade 3, others 0 or 1) or mild disability in three or four FS (three/four FS grade 2, others 0 or 1) though fully ambulatory.
- ☐ 3.5 = Fully ambulatory but with moderate disability in one FS (one grade 3) and one or two FS grade 2; or two FS grade 3 (other 0 or 1).
- ☐ 4.0 = Fully ambulatory without aid, self-sufficient, up and about some 12 hours a day despite relatively severe disability consisting of one FS grade 4 (other 0 or 1), or combinations of lesser grades exceeding limits or previous steps.
- ☐ 4.5 = Fully ambulatory without aid, up and about much of the day, able to work a full day, may otherwise have some limitation of full activity or require minimal assistance; characterized by relatively severe disability usually consisting of one FS grade 4 (others 0 or 1) or combinations of lesser grades exceeding limits of previous steps; able to walk without aid or rest some 300 M.
- ☐ 5.0 = Ambulatory without aid for at least 200 M; disability severe enough to impair full daily acitivities (e.g., to work a full day without special provisions). (Usual FS equivalents are one grade 5 above, others 0 or 1; combinations of lesser grades.)
- ☐ 5.5 = Ambulatory without aid for at least 100 M; diability severe enough to preclude fully daily activities. (Usual FS equivalents are on grade 5 above, others 0 or 1; or combinations of lesser grades.)
- ☐ 6.0 = Intermittent or unilateral constant assistance (cane, crutch, brace) required to walk at least 100 M. (Usual FS equivalents are combinations with more than one FS grade 3+.)
- ☐ 6.5 = Constant bilateral assistance (canes, crutches, braces) required to walk at least 20 M. (Usual FS equivalents are combinations with more than one FS grade 3+.)
- ☐ 7.0 = Unable to walk beyond approximately 5M even with aid, essentially restricted to wheelchair; wheels self and transfers alone; up and about in w/c some 12 hours a day. (Usual FS equivalents are combinations with more than one FS grade 4+; very rarely pyramidal grade 5 alone.)
- ☐ 7.5 = Unable to take more than a few steps; restricted to wheelchair; may need aid in transfer; wheels self but cannot carry on in w/c a full day; may need motorized wheelchair. (Usual FS equivalents are combinations with more than one FS grade 4+; very rarely pyramidal grade 5 alone.)
- ☐ 8.0 = Essentially restricted to bed or chair or perambulated in wheelchair, but out of bed most of day; retains many self care functions; generally has effective use of arms. (Usual FS equivalents are combinations, generally 4+ in several systems.)
- ☐ 8.5 = Essentially restricted to bed most of the day; has some effective use of arm(s); retains some self care functions. (Usual FS combinations generally 4+ in several systems.)
- ☐ 9.0 = Helpless bed patient; can communicate and eat. (Usual FS equivalents are combinations, mostly grade 4+.)
- ☐ 9.5 = Totally helpless bed patient; unable to communicate effectively or eat/swallow. (Usual FS equivalents are combinations mostly grade 4+.)
- ☐ 10.0 = Death due to MS.

FUNCTIONAL NEUROLOGICAL STATUS EVALUATION
Place an X in the box next to the description of the subject's level of function.

A. PYRAMIDAL FUNCTIONS
- ☐ 0 = normal
- ☐ 1 = abnormal signs without disability
- ☐ 2 = minimal disability
- ☐ 3 a. = mild or moderate paraparesis or hemiparesis
- ☐    b. = severe monoparesis
- ☐ 4 a. = marked paraparesis or hemiparesis

APPENDIX ONE-continued

☐ b. = moderate quadriparesis
☐ c. = monoplegia
☐ 5 a. = paraplegia
☐ b. = hemiplegia
☐ c. = marked quadriparesis
☐ 6 = quadriplegia, paralysis of 4 limbs

B. CEREBELLAR FUNCTIONS

☐ 0 = normal
☐ 1 = abnormal signs without disability
☐ 2 = mild ataxia
☐ 3 a. = moderate truncal ataxia
☐ b. = moderate limb ataxia
☐ 4 = severe ataxia all limbs
☐ 5 = unable to perform coordinated movements due to ataxia

C. BRAIN STEM FUNCTIONS

☐ 0 = normal
☐ 1 = signs only
☐ 2 a. = moderate nystagmus
☐ b. = other mild disability
☐ 3 a. = severe nystagmus
☐ b. = marked extraocular weakness
☐ c. = moderate disability of other cranial nerves
☐ 4 a. = marked dysarthria
☐ b. = other marked disability
☐ 5 = inability to swallow or speak

D. SENSORY FUNCTIONS

☐ 0 = normal
☐ 1 = vibration of figure-writing decrease only, in 1 or 2 limbs
☐ 2 a. = mild decrease in touch or pain or position sense-and/or moderate decrease in vibration in 1 or 2 limbs
☐ b. = vibratory (c/s figure writing) decrease alone in 3 or 4 limbs
☐ 3 a. = moderate decrease in touch or pain or position sense and/or essentially lost vibration in 1 or 2 limbs
☐ b. = mild decrease in touch or pain and/or moderate decrease in all proprioceptive tests in 3 or 4 limbs
☐ 4 a. = marked decrease in touch or pain or proprioception, alone or combined, in 1 or 2 limbs
☐ b. = moderate decrease in touch or pain and/or severe proprioceptive loss in more than 2 limbs
☐ 5 a. = loss (essentially) of sensation in 1 or 2 limbs
☐ b. = moderate decrease in touch or pain and/or loss of proprioception for most of the body below the head
☐ 6 = sensation essentially lost below the head

E. BOWEL AND BLADDER FUNCTIONS

☐ 0 = normal
☐ 1 = mild urinary hesitancy, urgency or retention
☐ 2 = moderate hesitance, urgency, retention of bowel or bladder or rary urinary incontinence
☐ 3 = frequent urinary incontinence
☐ 4 = in need of almost constant catheterization but with adequate bowel function
☐ 5 = loss of bladder function
☐ 6 = loss of bowel and bladder function

F. VISUAL FUNCTIONS

☐ 0 = normal
☐ 1 = scotoma with visual acuity (corrected) better than 20/30
☐ 2 = worse eye with large scotoma with maximal visual acuity (corrected) of 20/30 to 20/59
☐ 3 = worse eye with large scotoma, or moderate decrease in fields, but with maximal visual acuity (corrected)
☐ 4 = worse eye with marked decrease of fields and maximal acuity (corrected) or 20/100 to 20/200; grade 3 plus maximal acuity of better eye 20/60 or less
☐ 5 = worse eye with maximal visual acuity (corrected) less than 20/200; grade 4 plus maximal acuity of better eye 20/80 or less
☐ 6 = grade 5 plus maximal visual acuity of better eye 20/80 or less

G. MENTAL FUNCTIONS

☐ 0 = normal
☐ 1 = mood alteration only
☐ 2 = mild decrease mentation
☐ 3 = moderate decrease mentation
☐ 4 = marked decrease mentation (chronic brain syndrome, moderate)
☐ 5 a. = dementia
☐ b. = chronic brain syndrome, severe, incompetent

H. SPASTICITY

☐ 0 = none
☐ 1 = mild (detectable only)
☐ 2 = moderate (minor with function)
☐ 3 = severe (major interference with function)

I. OTHER FUNCTIIONS

☐ 0 = none
☐ 1 = any other findings (specify)

| SCRIPPS NEUROLOGICAL RATING SCALE WORKSHEET | | | | | |
|---|---|---|---|---|---|
| System Examined | Maximum Points | Normal | Mild | Moderate | Severe |
| Mentation and Mood | 10 | 10 | 7 | 4 | 0 |
| Cranial Nerves: | 21 | | | | |
| Visual Acuity | | 5 | 3 | 1 | 0 |
| Fields, Disks, Pupils | | 6 | 4 | 2 | 0 |
| Eye Movements | | 5 | 3 | 1 | 0 |

APPENDIX ONE-continued

| | | | | | |
|---|---|---|---|---|---|
| Nystagmus | | 5 | 3 | 1 | 0 |
| Lower Cranial Nerves | 5 | 5 | 3 | 1 | 0 |
| Motor: | | | | | |
| RU | 20 | 5 | 3 | 1 | 0 |
| LU | | 5 | 3 | 1 | 0 |
| RL | | 5 | 3 | 1 | 0 |
| LL | | 5 | 3 | 1 | 0 |
| DTRS: | | | | | |
| UE | 8 | 4 | 3 | 1 | 0 |
| LE | | 4 | 3 | 1 | 0 |
| Babinski: | 4 | 4 | | | 0 |
| R; L (2 ea.) | | | | | |
| Sensory: | | | | | |
| RU | 12 | 3 | 2 | 1 | 0 |
| LU | | 3 | 2 | 1 | 0 |
| RL | | 3 | 2 | 1 | 0 |
| LL | | 3 | 2 | 1 | 0 |
| Cerebellar: | | | | | |
| UE | 10 | 5 | 3 | 1 | 0 |
| LE | | 5 | 3 | 1 | 0 |
| Gait, Trunk and Balance | 10 | 10 | 7 | 4 | 0 |
| Special Category: | 0 | 0 | −3 | −7 | −10 |
| Bladder/Bowel/Sexual Dysfunction | | | | | |
| Totals: | 100 | | | | |
| | | Final Score | | | |

AMBULATION INDEX

☐ 0 = Asymptomatic; fully active
☐ 1 = Walks normally but reports fatigue which interferes with athletic or other demanding activities.
☐ 2 = Abnormal gait or episodic imbalance; gait disorder is noticeable to family and friends. Able to walk 25 feet in 10 seconds or less.
☐ 3 = Walks independently; able to walk 25 feet in 20 seconds or less.
☐ 4 = Requires unilateral support (cane, single crutch) to walk; used support more than 80% of the time. Walks 25 feet in 20 seconds or less.
☐ 5 = Requires bilateral support (canes, crutches, walker) and walks 25 feet in 20 seconds or less; or, requires unilateral support but walks 25 feet in greater than 20 seconds.
☐ 6 = Requires bilateral support and walks 25 feet in greater than 20 seconds. May use wheelchair on occasion.*
☐ 7 = Walking limited to several steps with bilateral support; unable to walk 25 feet. May use wheelchair for most activities.
☐ 8 = Restricted to wheelchair; able to transfer independently.
☐ 9 = Restricted to wheelchair; unable to transfer independently.

(*The use of a wheelchair may be determined by a patient's lifestyle and motivation. It is expected that patients in grade 7 will use a wheelchair more frequently than patients in grades 5 or 6. Assignment of a grade, however, in the 5-7 range is determined by the ability of a patient to walk a given distance and not by the extent to which a patient uses a wheelchair.)

_____ Total

Weiner HL and Ellison GW (1983). A working protocol to be used as a guideline for trials in multiple sclerosis. Arch Neurol 40:704-710.

APPENDIX TWO

STATISTICAL ANALYSES

Sample-Size Considerations

Chronic/Progressive Patients. The primary endpoint for this study in the group of patients with chronic/progressive disease will be the change in the Kurtzke disability status score from baseline to the final clinical evaluation at two years (Kurtzke, 1983). As discussed in the materials and methods section, we believe it is feasible to recruit and follow a total of 50-60 such patients over the course of this project. In order to determine the magnitude of the true treatment effect that we are likely to detect with a study of this size, an estimate of the variability in the change scores over a two-year period is needed. For patients with chronic/progressive disease it is postulated that, in the placebo group, the observed changes will range from a slight improvement of half a point (−0.5) to a worsening of at most 4.5 points. This would correspond to a range of values of 5 points [4.5−(−0.5)]. In the treated group, it is felt that the individual changes will range from −1.0 to +4.0, again a range of 5 points on the Kurtzke scale. Assuming that the individual changes are approximately normally distributed, this would correspond to a standard deviation, $\sigma$, in each group of about $5.0/4.0 = 1.25$. (Although, strictly speaking, the change score is an ordered categorical variable, this should provide a reasonable estimate. Even if the values were uniformly distributed over this range, the standard deviation would be 1.44, only slightly greater than the assumed 1.25.)

This estimate compares favorably with the findings of a two-year trial conducted by the Multiple Sclerosis Study Group (1990) comparing cyclosporine with placebo in chronic/progressive patients. In their study, the standard deviation of the change in score was 1.07 for cyclosporine-treated patients and 1.08 for placebo patients. Thus an assumed value of 1.25 seems reasonable and may even be a bit conservative.

Given this estimate of variability, with $n=25$ patients per treatment group, the standard error (SE) of the difference in the mean change scores will be, approximately, $$SE(\bar{d}_1-\bar{d}_2)=\sqrt{1.25^2/25+1.25^2/25}=0.354$$

The study will therefore have 80% power to detect a true difference, δ, in the mean change scores between the two groups of 2.8×0.354=0.990, i.e., about one unit on the Kurtzke disability scale. To allow for dilution of the treatment effect due to an anticipated dropout rate of 5%, a total of $25/(1-0.05)^2=28$ patients will be enrolled per treatment arm (Lachin, 1981).

Relapsing/Remitting Patients. In the relapsing/remitting stratum, the primary endpoint will be the number of exacerbations over the two-year treatment period. The entry criteria for these patients is four exacerbations over the previous two-year period. If we assume that, owing to a placebo effect, the untreated patients will experience an average of 3 exacerbations during the two-year trial period, and if we assume that the number of exacerbations follows a Poisson distribution, then the mean and standard deviation in the placebo group will be about 3 and $\sqrt{3}=1.7$, respectively. Further calculation shows that with n=25 patients per group, the study will have 80% power to detect a true reduction in the number of exacerbations from 3 in the placebo group to approximately 1.8 in the treated group, i.e., from a rate of 1.5 per year to 0.9 per year. As discussed above, a total of 28 patients per group will be entered to allow for a small number of dropouts.

Statistical Analysis

Preliminary analyses will compare the distributions of demographic and other baseline variables in the two treatment groups as a check on the validity of the randomization. For patients with chronic/progressive disease the mean change in the Kurtzke disability status score from baseline to two years will be compared between the two treatment groups by a two-sample t test. Analysis of covariance may also be performed to adjust for any chance imbalances in important prognostic variables at baseline. In addition, we will perform a Mann-Whitney nonparametric test; this test can be expected to yield results similar to the t test, but will also provide an estimate of the "probability of a better response to treatment than to placebo" (Moses et al., 1984). We will also conduct an analysis of variance of repeated measures using all of the serial data available from the baseline and followup examinations. Some of the various autoregressive models for longitudinal data (Rosner et al., 1985; Rosner and Munoz, 1988), as well as the approach to repeated measures proposed by Diggle (1988), may prove useful here.

In the relapsing/remitting patients the analysis will focus on the number of exacerbations observed during the two-year followup period. We will first test the assumption that the number of exacerbations follows a Poisson distribution and, if so, compare the mean rates in the two treatment groups. If the Poisson assumption is not valid, we will treat the number of events as an ordered categorical variable and perform a nonparametric Mann-Whitney test.

Secondary response variables will include the number of exacerbations in the chronic/progressive stratum, the change in the Kurtzke disability score in relapsing/remitting patients, the Ambulation Index, the Scripps Neurological Rating Scale, individual results from the functional neurological status evaluation, and the various laboratory tests and measures of immune response described in the materials and methods section. Similar statistical techniques will be applied to these data to assess the magnitude and significance of group difference. Finally, a method due to O'Brien (1984) will be used to combine the results from the various endpoints into a single summary measure that addresses whether or not the therapy is effective.

Monitoring Bounds

It is expected that recruitment of 112 patients (56 chronic/progressive and 56 relapsing/remitting) will take place over the first two years of the trial. During this period the data will be monitored periodically, primarily for evidence of toxicity or a significant worsening of condition associated with terbutaline. After recruitment is completed, formal O'Brien-Fleming (1979) monitoring bounds will be established. We will perform four sequential "looks" at the data, at six-month intervals beginning 2.5 months into the study. Assuming a uniform rate of entry of patients into the trial, these looks will be based on the two-year results in 28, 56, 84, and 112 patients, respectively. To allow for the multiple testing, the O'Brien-Fleming procedure uses rather conservative critical values initially; these taper off to a critical value for the final look that is not much greater than the nominal value of 1.96 appropriate for a single test at the end of the trial Diggle, P. (1988). An approach to the analysis of repeated measurements. *Biometrics* 44:959–971.

O'Brien, P. C. (1984). Procedures for comparing samples with multiple endpoints. *Biometrics* 40:1079–1087.

O'Brien, P. C. and Fleming, T. R. (1979). A multiple testing procedure for clinical trials. *Biometrics* 35:549–556.

Rosner, B., Munoz, A., Tager, I., Speizer, F., and Weiss, S. (1985). The use of an autoregressive model for the analysis of longitudinal data in epidemiologic studies. *Statistics in Medicine* 4:457–467.

Rosner, B. and Munoz, A. (1988). Autoregressive modelling for the analysis of longitudinal data with unequally spaced examinations. *Statistics in Medicine* 7:59–71.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

fiua, M. A., et al. (1987) "Sympathectomy enhances the severity of experimental autoimmune myasthenia gravis (EAMG)," *J. Neuroimmunol.*, 16:11–12.

Cartlidge, N. E. F. (1972) "Autonomic function in multiple sclerosis," *Brain*, 95:661–664.

Chagnac, Y., et al. (1986) "Paroxysmal atrial fibrillation associated with an attack of multiple sclerosis," *Postgrad. Med. J.*, 62:385–387.

Chelmicka-Schorr, E., et al. (1988) "Chemical sympathectomy augments the severity of experimental allergic encephalomyelitis," *J. Neuroimmunol.*, 17:347–350.

Ehelmicka-Schorr, E., et al. (1989a) "Treatment with β-adrenergic agonist isoproterenol protects against development of experimental allergic encephalomyelitis (EAE) in rats," *Neurology* 39 (Suppl 1):330.

Chelmicka-Schorr, E., et al. (1989b) "The β-adrenergic agonist isoproterenol suppresses experimental allergic encephalomyelitis in Lewis rats," *J. Neuroimmunol.*, 25:203–207.

Desmedt, J. E. (1981a) "How to validate myasthenia gravis in the patient with a diagnostic problem," *Ann NY Acad Sci*, 377:583–605.

Desmedt, J. E. (1981b), "Plasticity of motor unit organization studied by coherent electromyography in patients with nerve lesions or with myopathic or neuropathic diseases," In: *Motor Unit Types, Recruitment and Plasticity in Health and Disease: Progress in Clinical Neurophysiology* (Desmedt, J. E., ed), 9:250–304.

Desmedt, J. E. (1981c) "The electrophysiological validation of myasthenia in the patient with a diagnostic problem," In: *Gravis* (Eldefrawi, A. T., Albuquerque EX, eds), Chapman and Hall, London.

Felten, D. L., et al. (1987a) "Noradrenergic sympathetic neural interactions with immune system: Structure and function," *Immunol. Rev.*, 100:225–260.

Felten, D. L., et al. (1987b) "Noradrenergic sympathetic innervation of the spleen: I. Nerve fibers associate with lymphocytes and macrophages in specific compartments of the splenic white pulp," *J. Neurosci. Res.*, 18:28–36.

Fierz, W., et al. (1985) "Astrocytes as antigen-presenting cells. I. Induction of Ia antigen expression on astrocytes by T cells via immune interferon and its effect on antigen presentation," *J. Immunol.*, 134:3785–3793.

Giron, L. T., et al. (1980) "Lymph nodes: A possible site for sympathetic neuronal regulation of immune responses," *Ann. Neurol.*, 8:520–525.

Gomez, C., et al. (1979) "Monoclonal antibodies against purified nicotinic acetylcholine receptor," *Biochem, Biophys, Res. Commun.*, 88:575–582.

Hadden, J. W. (1975) "Cyclic nucleotides inn lymphocyte function," *Ann. N.Y. Acad. Sci.*, 256:256–363.

Karaszewski, J. W., et al. (1990) "Sympathetic skin responses are decreased and lymphocyte beta-adrenergic receptors are increased in progressive multiple sclerosis," *Ann. Neurol.*, 27:366–372.

Karaszewski, J. W., et al. (1991) "Increased lymphocyte beta-adrenergic receptor density in progressive multiple sclerosis is specific for the CD8+, CD28− suppressor cell," *Ann. Neurol.*, 30:42–47.

Krueger et al., (1984) "Muramyl peptides. Variation of somnogenic activity with structure," *J. Exper. Med.*, 159:68–76.

Kurtzke, J. F., et al. (1983) "Rating neurologic impairment in multiple sclerosis: an expanded disability status scale (EDSS). *Neurology*, 33:1444–1452.

Lachin, J. M., et al. (1988) "Randomization in Clinical Trials: Conclusions and Recommendations," *Controlled Clinical Trials*, 9:365–374.

Lefkowitz, R. J., et al. (1981) "Molecular pharmacology of adenylate cyclase-coupled α- and β-adrenergic receptors," *Adv. Cyclic Nucl. Res.*, 14:145–161.

Lennon, V. A., et al. (1975) "Experimental autoimmune myasthenia: a model in rats and guinea pigs," *J. Exp. Med.*, 141:1365–1375.

Lennon, V. A., et al. (1976) "Experimental autoimmune myasthenia gravis: cellular and humoral immune responses," *Ann. NY Acad. Sci.*, 274:283–299.

Lennon, V. A., et al. (1980) "Myasthenia gravis induced by monoclonal antibodies to acetylcholine receptors," *Nature*, 285:238–240.

Lindstrom, J., et al. (1976) "Pathological mechanisms in experimental autoimmune myasthenia gravis: II. Passive transfer of experimental autoimmune myasthenia gravis in rats with antiacetylcholine receptor antibodies," *J. Exp. Med.*, 144:739–753.

Mackenzie, F. J., et al. (1989) "Changes in lymphocyte β-adrenergic receptor density and noradrenaline content of the spleen are early indicators of immune reactivity in acute experimental allergic encephalomyelitis in the Lewis rat," *J. Neuroimmunol.*, 23:93–100.

McFarlin, D. E. (1985) "Use of interferon in multiple sclerosis," *Ann. Neurol.*, 18:432.

Miles K., et al. (1981a) "The sympathetic nervous system modulates antibody response to thymus-independent antigens," *J. Neuroimmunol*, 1:101–105.

Miles, K., et al. (1981b) "Immune regulation by the sympathetic nervous system," *Neurology*, 31(2):137.

Miles, K. (1984) "The sympathetic nervous system and the immune response in mice," Ph.D. Dissertation, University of Chicago, Chicago, Ill.

Miles, K. et al. (1984) "Sympathetic nervous system and immune response in mice," *Neurology*, 34(Suppl 1):259.

Murphy, P. A., et al. (1980) "Endogenous pyrogens made by rabbit peritoneal exudate cells are identical with lymphocyte-activating factors made by rabbit alveolar macrophages," *J. Immunol.*, 124:2498–2501.

Neubauer, B. and Gundersen, H. J. G. (1978) "Analysis of heart rate variations in patients with multiple sclerosis," *J. Neurol. Neurosur. Psychiat.*, 41:417–419.

Nordenbo, A. M. (1988) "Autonomic dysfunction in multiple sclerosis patients with special reference to sweating response," *Elsevier Sci. Pub.*, p.402.

Noronha, M. J., et al. (1968) "Autonomic dysfunction (sweating responses) in multiple sclerosis," *J. Neurol. Neurosurg. Psychiat.*, 31:19–22.

Osserman, K. E., et al. (1958). In: *Myasthenia Gravis*, Grune & Stratton, New York, pp. 79–86.

Pentland, B. and Ewing, D. J. (1987) "Cardiovascular reflexes in multiple sclerosis," *Eur. Neurol.*, 26:46–50.

Poser, C. M., et al. (1983) "New diagnostic criteria for multiple sclerosis: guidelines for research protocols," *Ann. Neurol*, 13:227–231.

RAND Corp. (1955) *A Million Random Digits with 100,000 Normal Deviates*, New York: The Free Press.

Reder, A. T. and Arnason B. G. W. (1985) "Immunology of multiple sclerosis," *Handbook of Clinical Neurology*, Vinken, P. J., Bruyn, G. W., Klawans, H. L., and Koetsier, J. C. (eds), Elsevier Science Publishers, Amsterdam, pp. 337–395.

Reilly, F. D., et al. (1976) "Studies of the hemopoietic microenvironment. VIII. Adrenergic and cholinergic innervation of the murine spleen," *Anat. Rec.*, 105:100.

Schumacher, G. A. et al. (1965) "Problems of experimental trials of therapy in multiple sclerosis: report by the panel on the evaluation of experimental trials of therapy in multiple sclerosis," *Ann. N.Y. Acad. Sci.*, 122:552–568.

Senaratne, M. P. J., et al. (1984) "Evidence for cardiovascular autonomic nerve dysfunction in multiple sclerosis," *J. Neurol. Neurosurg. Psychiat.*, 47:947–952.

Sterman, A. B., et al. (1985) "Disseminated abnormalities of cardiovascular autonomic functions in multiple sclerosis," *neurology*, 35:1665–1668.

Tarrab-Hazdai, R., et al. (1975) "Experimental autoimmune myasthenia induced in monkeys by purified acetylcholine receptor, " *Nature*, 256:128–130.

Weiner, H. L. & Ellison (1983) *Arch. Neurol.*, 40:704–710.

Williams, J. M., et al. (1981) "Sympathetic innervation of murine thymus and spleen: Evidence for a functional link between the nervous and immune systems," *Brain Res. Bell.*, 6:83–94.

Yam, L. T. et al. (1971) "Cytochemical identification of monocytes and granulocytes," *Am. J. Clin. Pathol.*, 55:283–290.

What is claimed is:

1. A method of treating demyelinating disease or autoimmune disease in a patient comprising administering to the patient a therapeutically effective dose of a $\beta_2$-adrenergic agonist selected from the group consisting of terbutaline, metaproterenol, albuterol, isoetharine, pirbuterol, bitolterol and ritodrine in a pharmaceutically acceptable vehicle.

2. The method of claim 1, wherein the $\beta$-adrenergic agonist is administered in an oral or parenteral dosage form.

3. The method of claim 2, wherein the dosage form is a sustained release form.

4. The method of claim 1, wherein the dose comprises from about 1 mg to about 10 mg of the $\beta$-adrenergic agonist.

5. The method of claim 4, wherein the dose comprises from about 2 mg to about 5 mg of the $\beta$-adrenergic agonist.

6. The method of claim 5, wherein the dose comprises from about 1.25 mg to about 2.5 mg of the $\beta$-adrenergic agonist.

7. The method of claim 1, wherein the patient suffers from a demyelinating disease.

8. The method of claim 7, wherein the patient has multiple sclerosis, post-infectious encephalomyelitis, inflammatory demyelinating polyneuropathy, or acute inflammatory demyelinating polyradiculoneuropathy.

9. The method of claim 1, wherein the patient has myasthenia gravis.

* * * * *

UNITED STATES PATENT AND TRADEMARK OFFICE
CERTIFICATE OF CORRECTION

PATENT NO. : 5,264,459
DATED : November 23, 1993
INVENTOR(S) : Chelmicka-Schorr et al It is certified that error appears in the above-indentified patent and that said Letters Patent is hereby corrected as shown below:

In claim 2, line 3, column 26, delete "B" and substitute -- $B_2$ --.

In claim 4, line 9, column 26, delete "B" and substitute -- $B_2$ --.

In claim 5, line 12, column 26, delete "B" and substitute -- $B_2$ --.

In claim 6, line 16, column 26, delete "B" and substitute -- $B_2$ --.

Signed and Sealed this

Third Day of May, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,264,459

DATED : November 23, 1993

INVENTOR(S) : Chelmicka-Schorr *et al.*

It is certified that error appears in the above-indentified patent and that said Letters Patent is hereby corrected as shown below:

In column 2, line 24, replace "CAMP" with --cAMP--.

In column 5, line 57, replace "effeot" with --effect--.

In column 6, line 33, replace "Student" with --Student's--.

In column 6, line 33, delete the "," after "Students".

In column 6, line 67, replace "patients" with --patient's--.

In column 6, line 67, delete "," after --patients--.

In column 7, line 7, replace "Were" with --were--.

In column 7, line 44, replace "Weeks" with --weeks--.

In column 8, line 49, delete ----- after "chronic/".

In column 9, line 57, replace "KurtZke" with --Kurtzke--.

In column 10, line 45, delete "is".

In column 12, line 23, replace "t achycardia" with --tachycardia--.

In column 13, line 5, replace "induoe" with --induce--.

In column 13, line 8, replace "californica" with --*californica*--.

UNITED STATES PATENT AND TRADEMARK OFFICE
CERTIFICATE OF CORRECTION

PATENT NO. : 5,264,459
DATED : November 23, 1993
INVENTOR(S) : Chelmicka-Schorr et al.

It is certified that error appears in the above-indentified patent and that said Letters Patent is hereby corrected as shown below:

In column 6, line 48, replace "0.001" with --0.01--.

In column 7, line 7, insert --t-- after "Sal".

In column 7, line 25, insert -- = -- between the "dl".

In column 7, line 26, insert --was-- after "tion".

In column 8, line 54, insert --/-- after "chronic".

In column 8, line 63, replace "with in" with --within--.

In column 9, line 19, replace the second "and" with --on--.

In column 9, line 44, insert --,-- after "asthma".

In column 9, line 64, insert --,-- after "Chem-17".

In column 10, line 24, insert --,-- after "18".

In column 10, line 44, insert --,-- after "Chem-17".

In column 10, line 49, insert --,-- after "12".

In column 11, line 24, replace "$10_6$" with --$10^6$--.

In column 11, line 27, replace "$cm_2$" with --$cm^2$--.

In column 11, line 29, replace "of" with --or--.

In column 11, line 33, replace "106" with --$10^6$--.

UNITED STATES PATENT AND TRADEMARK OFFICE
CERTIFICATE OF CORRECTION

PATENT NO. : 5,264,459  
DATED : November 23, 1993  
INVENTOR(S) : Chelmicka-Schorr *et al.*

It is certified that error appears in the above-indentified patent and that said Letters Patent is hereby corrected as shown below:

In column 11, line 35, replace "$10_6$" with --$10^6$--.

In column 13, line 23, replace "Introduction" with --Induction--.

In column 13, line 44, insert --t-- before "test".

In column 15, line 16, replace "weighted" with --weighed--.

In column 15, line 19, add --al,-- to the word "physiologic".

In column 22, line 46, insert --,-- after "methods".

In column 22, line 49, insert --,-- after "spirit".

In column 23, line 49, replace "inn" with --in--.

In column 24, line 49, replace "Myasthenia Gravis" with --*Myasthenia Gravis*--.

In column 24, line 60, insert --Vol. 47-- after "*rology*".

In column 25, line 8, replace "*neurology*" with --*Neurology*--.

In column 25, line 12, insert --G.W.-- after "Ellison".

In column 25, line 12, insert --A working protocol to be used as a guideline for trials in multiple sclerosis--.

In column 26, line 1, insert --,-- after "bitolterol".

UNITED STATES PATENT AND TRADEMARK OFFICE
CERTIFICATE OF CORRECTION

PATENT NO. : 5,264,459

DATED : November 23, 1993

INVENTOR(S) : Chelmicka-Schorr et al.

It is certified that error appears in the above-indentified patent and that said Letters Patent is hereby corrected as shown below:

In column 22, line 64, replace "fiua" with --Aqius--.

In column 23, line 8, replace "Ehelmicka-Schorr" with --Chelmicka-Schorr--.

In column 23, line 28, insert --Fundamentals of Neuromuscular Transmission and Myasthemia-- after "*In:*".

In column 24, line 52, replace "Eur. Neurol." with --*Eur. Neurol*--.

In column 1, line 19, insert --,-- after "polyradiculoneuropathy".

In column 2, line 6, insert --s-- after "response".

In column 3, line 15, insert --,-- after "plasmapheresis".

In column 3, line 19, insert --,-- after "diarrhoea".

In column 3, line 21, insert --,-- after "damage".

In column 4, line 9, delete the second "are known by those".

In column 5, line 55, replace "CAMP" with --cAMP--.

In column 5, line 61, insert --s-- after "disease".

UNITED STATES PATENT AND TRADEMARK OFFICE
CERTIFICATE OF CORRECTION

PATENT NO. : 5,264,459
DATED : November 23, 1993
INVENTOR(S) : Chelmicka-Schorr et al.

It is certified that error appears in the above-indentified patent and that said Letters Patent is hereby corrected as shown below:

In column 6, line 33, replace "t-test" with --t test--.

Signed and Sealed this

Fourth Day of October, 1994

Attest:

BRUCE LEHMAN

Attesting Officer

Commissioner of Patents and Trademarks